(12) United States Patent
Curry

(10) Patent No.: US 9,182,334 B2
(45) Date of Patent: Nov. 10, 2015

(54) METHOD OF DETERMINING THERMODYNAMIC AND KINETIC PARAMETERS FROM MEASURED OFF RATES

(71) Applicant: Agilent Technologies, Inc., Santa Clara, CA (US)

(72) Inventor: Bo Curry, Redwood City, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 12 days.

(21) Appl. No.: 13/758,708

(22) Filed: Feb. 4, 2013

(65) Prior Publication Data

US 2013/0225429 A1    Aug. 29, 2013

Related U.S. Application Data

(60) Provisional application No. 61/644,307, filed on May 8, 2012, provisional application No. 61/603,041, filed on Feb. 24, 2012.

(51) Int. Cl.
| | | |
|---|---|---|
| *G01N 33/48* | (2006.01) | |
| *G01N 33/53* | (2006.01) | |
| *G01N 19/04* | (2006.01) | |
| *C12Q 1/68* | (2006.01) | |
| *G01N 33/557* | (2006.01) | |

(52) U.S. Cl.
CPC .............. *G01N 19/04* (2013.01); *C12Q 1/6883* (2013.01); *G01N 33/557* (2013.01)

(58) Field of Classification Search
None
See application file for complete search history.

(56) References Cited

U.S. PATENT DOCUMENTS

| 5,445,971 A * | 8/1995 | Rohr ............................. 436/526 |
| 6,180,418 B1 * | 1/2001 | Lee ............................... 436/526 |
| 2010/0137120 A1 * | 6/2010 | Wong et al. .................... 494/10 |

FOREIGN PATENT DOCUMENTS

| WO | WO2010065477 | 6/2010 |
| WO | WO2011153211 | 12/2011 |

OTHER PUBLICATIONS

Halvorsen, et al., "Massively Parallel Single-Molecule Manipulation Using Centrifugal Force.", Biophysical Journal vol. 98, Jun. 2010, L53-L55.

* cited by examiner

*Primary Examiner* — Betty Forman

(57) ABSTRACT

A method for measuring a property of a binding interaction between a capture agent and a binding partner for the capture agent is provided. In certain embodiments, this method comprises: a) contacting a population of particles that are linked to a capture agent with a substrate comprising a binding partner to produce capture agent/binding partner complexes, wherein the population of particles comprises first particles that are bound to a single molecule of the capture agent and second particles that are bound to two molecules of the capture agent; b) applying a force to the bound support, wherein the force is in a direction that separates the particles from the support; and c) separately measuring the forces required to disassociate the first particles and the second particles from their respective complexes.

11 Claims, 3 Drawing Sheets

METHOD OF DETERMINING THERMODYNAMIC AND KINETIC PARAMETERS FROM MEASURED OFF RATES

CROSS-REFERENCING

This application claims the benefit of provisional application Ser. No. 61/603,041, filed Feb. 24, 2012, and provisional application Ser. No. 61/644,307, filed May 8, 2012, which are incorporated herein by reference.

INTRODUCTION

Many biochemical reactions involve specific non-covalent interactions between macromolecules, such as antibody antigen binding, DNA hybridization, and the like. In a typical binding reaction, a capture agent (e.g., a protein such as an antibody, or a nucleic acid) binds to a binding partner for the capture agent (e.g., which can be a protein or nucleic acid). To efficiently design and optimize artificial systems of biological macromolecules, and to improve our understanding of native biological systems, it is often useful to characterize the kinetics and thermodynamics of the target-probe interaction.

DESCRIPTION OF EXEMPLARY EMBODIMENTS

Figure 1:
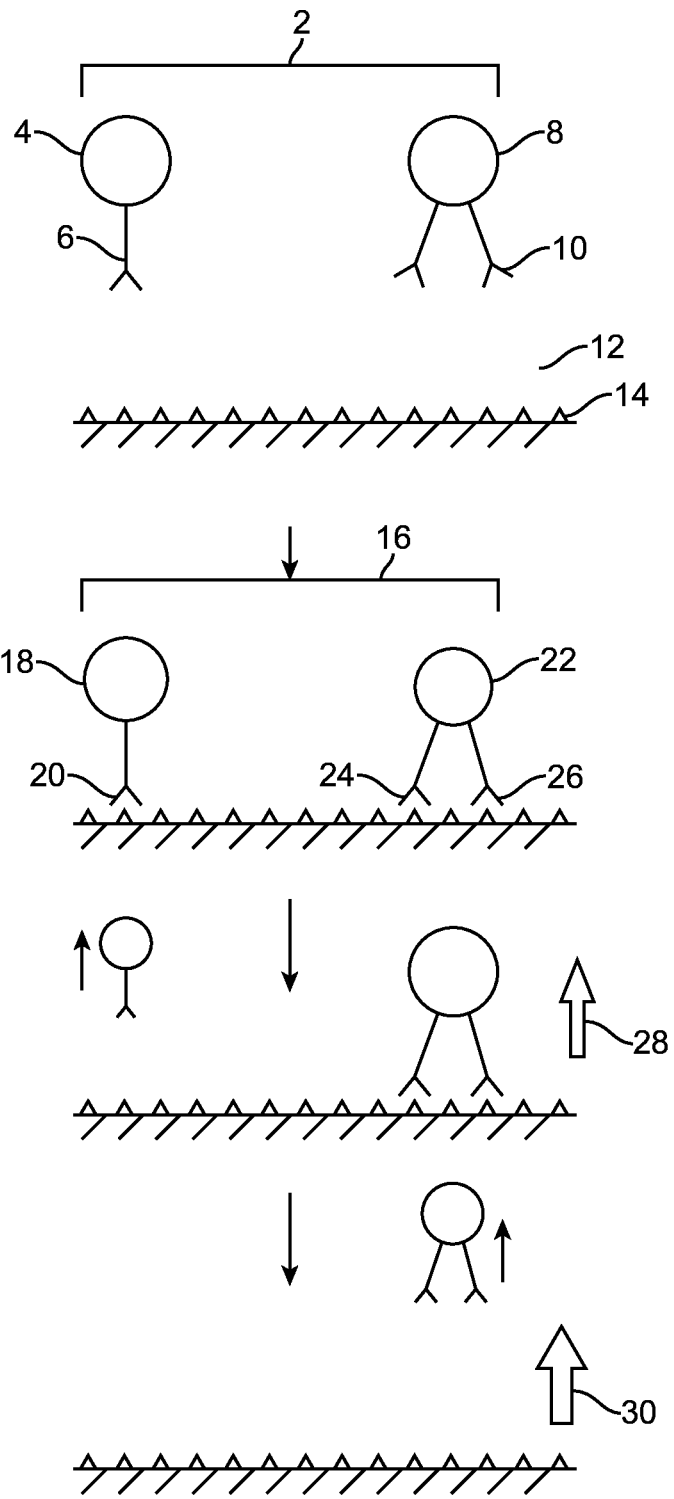
FIG. 1 schematically illustrates an exemplary embodiment of the method.

Before the present invention is described, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

A method for measuring a property of a binding interaction between a capture agent and a binding partner for the capture agent is provided. In certain embodiments, this method comprises: a) contacting a population of particles that are linked to a capture agent with a substrate comprising a binding partner to produce capture agent/binding partner complexes, wherein the population of particles comprises first particles that are bound to a single molecule of the capture agent and second particles that are bound to two molecules of the capture agent; b) applying a force to the bound support, wherein the force is in a direction that separates the particles from the support; and c) separately measuring the forces required to disassociate the first particles and the second particles from their respective complexes. In some cases, the applying comprises increasing the force over a period of time, and observing the release of the particles from the support.

FIG. 1 illustrates certain principles of the method. With reference to FIG. 1, a population of particles 2 that comprises first particles 4 that are bound to a single molecule of a capture agent band second particles 8 that are bound to two molecules of the capture agent 10 are contacted with a substrate 12 that has a binding partner 14 for the capture agent (i.e., a target molecule to which the capture agent binds, specifically or non-specifically) under conditions suitable for binding of the capture agent to the binding partners on the substrate. This step of the method results in the production of capture agent/binding partner complexes 16 that are bound to a substrate. As illustrated, some of the first particles, e.g., 18, are bound to the substrate via by a single (i.e., one) capture agent/binding partner interaction 20, and some of the second particles, e.g., 22 are bound to the substrate via by two (i.e., exactly two) capture agent/binding partner interactions 24 and 26. After the capture agent/binding partner complexes are formed and the unbound particles are washed from the substrate, a force that is in a direction that separates the particles from the support is applied. This force may be centrifugal or magnetic, although another type of force may be applied in certain cases. In general terms, after the force is applied, the force is increased and the forces required to disassociate the first particles 18 and the second particles 22 from their respective complexes are measured. More specifically, the force is increased, and the first particles that are bound to the substrate via by a single capture agent/binding partner interaction (i.e., particles 18) are released at first force 28. After the first particles are released, the force is increased and the second particles that are bound to the substrate via by two capture agent/binding partner interaction (i.e., particles 22) are released at second force 30. In certain embodiments, applying the force comprises increasing the force over a period of time, and observing, e.g., using an optical detection system, the release of the first and second particles from the support. The off rate for the first particles and the off rate for the second particles can be calculated using the forces required to release those particles from the substrate, and the on rate of the binding interaction can be calculated using the off rates for the first and second particles. In certain cases, the population of particles may also contain particles that are bound to three, four or five or more molecules of the capture agent. As such, in addition to there being particles bound to the substrate via by one or two interactions as described above the substrate may also contain further particles that are bound to the substrate by more than two interactions, e.g., 3, 4 or 5 interactions. If the force is increased sufficiently, the further particles, i.e., those that are bound by 3, 4, or 5 interactions, can be released, and the force required to release the further particles from the substrate can be determined. The off-rates for those particles can be calculated, and those off rates can also be used to calculate the on rate of the interaction in a similar manner as to that described below. The population of particles may also contain particles that are not bound to the capture agent. These particles should be released from the substrate at a very low force.

If a centrifugal system such as that described in Halvorsen et al (Biophys. J. 2010 98: L53-L55) is employed, the substrate rotates at angular velocity w and at a distance R from the center of axis. When the first and second particles undergo circular motion, a centripetal force F is exerted on the particles, as defined by the following equation:

$$F = \frac{mv^2}{R}$$

where F is the net centripetal force, m and v are the mass and the linear velocity of the particles, respectively, and R is the distance of the particles from rotation axis. In a rotating reference frame in which orbiting particles appears stationary, the particles experience an inertial centrifugal force equal to F in a direction perpendicular to outer surface and away from central axis (as shown by arrows 28 and 30 in FIG. 1). In some examples where the particles are spherical beads in solution with radius r and relative density p, rewriting the above equation in terms of angular velocity ω yields:

$$F = \frac{4\pi\rho r^3 R\omega^2}{3}$$

When the substrate rotates about its axis at a very low speed, centrifugal force F is countered by the force of the interaction between the capture agents and their binding partners, allowing the particles to continue to adhere to the substrate. As the rotational speed ω rises, the increasing magnitude of centrifugal force F causes the beads to move with respect to the substrate. The characteristics of the relative motion (e.g., the root-mean-square displacement or the direction of the motion) can be monitored and analyzed to quantify certain chemical and/or mechanical properties of the non-covalent bonds between the capture agents and their binding partners. The increasing F causes non-covalent bonds to break, at which point, a particle is released from surface. The magnitude of the centrifugal force F required to release the first particles is the force required to disassociate a single interaction, thereby allowing a disassociation constant of that interaction to be calculated. The log of the $k_{off}$ is approximately linear in the applied force, so the $k_{off}$ can be estimated by extrapolating the results obtained to a force of zero. After the first particles are released from the substrate the force is increased, and the force required to release the second particles is measured. The force required to release the second particles (which are linked to the substrate by two interactions) is disproportionate to (i.e., requires more than twice the force than) that required to release the first particles. This disproportionality is related to the association constant $k_{on}$ and is caused by capture agent/binding partner interactions being reformed after they have been broken. Stated a different way and with reference to FIG. 1, the rate at which the second particle is released is not only dependent on the rate at which interactions 24 and 26 are broken, but also on the rate at either of those interactions is re-formed while the other interaction is still intact. Thus, in certain cases, the on rate for the interaction can be calculated from the off rates. In certain cases, the method may further comprise calculating the off rate for the first particles and the off rate for the second particles, using the first and second forces measured above.

The cooperative binding of N identical capture agents can be modeled as a series of coupled differential equations:

$$f_N' = -Nk_1 f_N + k_2 f_{N-1} \qquad (1)$$

$$f_m' = -mk_1 f_m + (N-m+1)k_2 f_{m-1} + (m+1)k_1 f_{m+1} - (N-m)k_2 f_m$$
$$(1<m<N)$$

$$f_1' = k_1 f_1 + 2k_1 f_2 - (N-1)k_2 f_1$$

$$f_0' = k_1 f_1$$

where N is the total number of tethered captured agents on the beads, $f_m$ is the fraction of beads for which m of the N capture agents are bound, $f_m'$ is the time derivative of this fraction, $k_1$ is the off rate ($\sec^{-1}$) of a single tether under the applied force, and $k_2$ is the constant pseudo-first-order on-rate given by:

$$k_2 = ck_{on}, \qquad (2)$$

where c is the molar concentration of binding partner accessible to capture agents on a particle, which is essentially the number of moles of (surface bound) binding partner divided by the effective volume accessible to the bound capture agent. The volume accessible to the capture agent can be estimated as the volume of a hemisphere whose radius is the mean tether length, and the area of the surface accessible to the capture agent can be estimated as the area of a circle whose diameter is the bead diameter. The surface density of binding partners can be determined from other experiments, so the effective concentration can be estimated. Both of these estimates are independent of the nature of the capture agent and binding partner, and can therefore be refined empirically.

The capture agent and the binding partner used in the method may be any suitable molecule that is capable of binding to another molecule. Capture agents include any molecule (e.g., a polypeptide or polynucleotide, which could be RNA or DNA) that is capable of specifically binding to another molecule (a polypeptide or polynucleotide). Antibodies, transcription factors, oligonucleotides, and other proteins that contain domains that are known to interact with other molecules (via intra- or inter-molecular interactions), e.g., proteins that contain α-helical binding domains (e.g., ankyrin repeat proteins and leucine-rich repeat proteins), proteins that have a binding domain with an irregular secondary structure (e.g., PDZ proteins) and proteins that have a binding domain with a β-sheet structures, as described in Hosse, supra, are examples of suitable binding partners. Many other examples of capture agents are described in the literature. Likewise, the binding partner used may be any molecule that binds to the capture agent. Exemplary capture agent/binding partner pairs include: an antibody and an antigen, an oligonucleotide and the complement of the oligonucleotide, and a sequence specific RNA binding protein and its binding site. Conditions suitable for binding, e.g., proteins to other proteins or to nucleic acid, or for nucleic acid hybridization, are well known in the art. Methods for linking molecules to a support, e.g., a particle, e.g., a bead or a glass slide, etc., are well known in the art. A molecule can be tethered to a substrate using a suitable linking agent that generally possesses the following features, in order: a tag for linking to a substrate, a spacer moiety and a reactive group for linking to the molecule. The tag may be an affinity tag, e.g., a biotin group or the like, or a reactive moiety (e.g. a carboxy group, an amino group, a halo group, a tosylate group, a mesylate group, a reactive hydroxyl groups or metal oxide) that can react with suitable sites (e.g., alcohols, amino nucleophiles, thiol nucleophiles or silane groups) on the surface of a substrate to produce a covalent bond between the substrate and the linker. The spacer may contain an unreactive alkyl chain, e.g., containing 3-50 carbon atoms and may be chosen as containing appropriate chemistry. On one embodiment, an oligonucleotide linker (e.g., from 10 to 30 nucleotides in length) may be used. The tether should be flexible and of defined length, thereby allowing the effective concentration of the capture agent to be calculated and/or calibrated. The reactive group generally reacts with the molecule and forms a covalent bond therewith. The reactive group is selectively reactive with particular chemical groups in the capture agent. Suitable reactive groups include halogens (that are sulfhydryl reactive), N-hydroxysuccinimide (NHS)-carbonate (that are amine-reactive) and N,N-diisopropyl-2-cyanoethyl phosphoramadite (that are hydroxyl-reactive), and several other reactive groups are known in the art and may be readily employed in the instant methods. The substrate may be a nucleic acid array, e.g., a DNA or RNA array.

The particles used can range in size from 20 nM to 200 μM or larger, and may be made of polystyrene, but other materials such as polymethylmethacrylate (PMMA), polyvinyltoluene (PVT), styrene/butadiene (S/B) copolymer, styrene/vinyltoluene (S/VT), may also be used. The particles can be made to display a variety of chemically functional groups on their surface. Reactive groups commonly used include carboxyl, amino, aldehyde, hydroxyl, epoxy, and chloromethyl (See, e.g., U.S. Pat. Nos. 4,217,338, 5,326,692, 5,786,219, 4,717, 655, 7,445,844 5,573,909 and 6,023,540) To these reactive groups other types of linkers can be attached. Beads as described above can be obtained commercially from numerous sources. In general terms, the population of particles used in practicing should be of a uniform size and density. Borosilicate glass, polystyrene, silica, gold, melamine or iron oxide particles can be made with defined size and density. For example, borosilicate particles have a density of 1.5 $g/cm^3$ and can be fabricated in any defined size in the following range: 1-100+μm; polystyrene particles have a density of 0.05 $g/cm^3$ and can be fabricated in any defined size in the following range 0.05-100+μm; silica particles have a density of 1.2 $g/cm^3$ and can be fabricated in any defined size in the following range 0.01-100 μm; gold particles have a density of 18.3 $g/cm^3$ and can be fabricated in any defined size in the following range 0.002-0.25 μm; melamine particles have a density of 0.51 $g/cm^3$ and can be fabricated in any defined size in the following range 0.5-10 μm; and iron oxide particles have a density of 4.24 $g/cm^3$ and can be fabricated in any defined size in the following range 1-10 μm.

The first particles (i.e., the particles that are bound to a single molecule of a capture agent 6 and second particles (i.e., the particles that are bound to two molecules of the capture agent) may be made by, e.g., making a dilution series of capture agent, reacting each of the dilutions with the particles, and then empirically determining which of the dilutions results in a composition containing an appropriate mix of first and second particles. For example, the ratio between the first particles and the second particles, or between the second particles or the first particles, may be pre-selected at approximately 1:2, 2:3, 3:4, 4:5, 5:6, 6:7, 7:8, 8:9, 9:10, 10:11, or 1:1, where a pre-selected ratio is one that is known it is understood that the actual ratio in the mix may deviate from the pre-selected ratio within routine operational errors. Reactive groups on the particles can be capped using known methods. Thus, also provided is a composition comprising a population of particles that are linked to a capture agent, wherein the population of particles comprises first particles that are bound to a single molecule of the capture agent and second particles that are bound to two molecules of the capture agent.

The type of force used to perform the analysis described above may be, e.g., centrifugal or magnetic. In embodiments in which centrifugal force is used, a spinning force microscope described by Halvorsen et al (Biophys. J. 2010 98: L53-L55) may be used. A spinning force microscope may comprise a rotary arm mechanically coupled to a rotary stage configured to rotate about a central axis at an adjustable angular velocity w. The rotary stage may be housed and supported on a stationary base immobilized on a platform such as a vibration-free optical table. The motion of rotary stage about central axis is computer controlled.

The rotary arm extends radially outward from central axis to support a set of optical, mechanical, and electrical components for detecting characteristics (e.g., motion, optical, and geometric characteristics) of a sample (which contains the substrate described above) to be measured. These components include, for example, a light source, an objective lens, a light detector, and a media converter. In operation, these components are moved by rotary arm to rotate about central axis at the same angular velocity w. Rotary arm may also carry one or more positioning elements for adjusting the position of each component coupled to arm.

In one configuration, a light source (e.g., a LED, xenon arc lamp or laser) is mounted at a distal end of rotary arm for emitting a light beam to illuminate a selected region of a substrate. Light source may also include a set of optical components such as lenses, mirrors, and filters for controlling the characteristics of its outgoing beam.

A substrate may be mounted onto the rotary arm with a sample holder and fastened to the arm. Depending on the particular implementation, the substrate may include an sample chamber in which the particles are sealed. The sample chamber may in certain cases consist of two parallel cover glasses separated by a 1 mm o-ring, forming an enclosed volume that can be filled with buffer and particles. In some implementations, the substrate may be oriented such that the surfaces of the cover glasses are aligned in parallel to central axis. When the rotary arm rotates, the contents of the sample experience a centrifugal force normal to the cover glasses. In other implementations, sample may be oriented at a selected (and possibly adjustable) angle with respect to central axis, enabling the centrifugal force to be applied in any given direction.

A light beam exiting the substrate is received by an objective lens to produce a real image of the illuminated region of the sample. In some cases, the relative position of the objective lens with respect to the substrate may be adjustable in three dimensions (x-, y- and z-directions), allowing images of different regions of the sample to be collected at various focal depths.

Images formed by the objective lens are received by a detector (e.g., a CCD or CMOS detector and subsequently converted into electronic signals. The detector may be capable of acquiring successive images at a speed sufficiently fast to enable video tracking of the sample at a high temporal resolution (e.g., 1 kHz). Electronic signals from the detector are delivered, for example, using electrical, optical, or wireless transmission means, to be passed onto a computer. Using proper interfacing software, the computer decodes the electronic signals from a media converter to reproduce images of the sample on a screen. The computer may be is used for viewing and processing images of sample. In addition, the computer may be configured to provide various control signals to control individual components of the spinning force microscope. For example, the computer may be coupled to an electric motor for controlling a rotational drive force to change the angular speed w of the rotary stage. The computer may also be coupled to a positioning device for adjusting the distance between the light source and the sample, or coupled to a positioner for translating the objective lens in each of x-, y-, and z-directions to select detection regions and to control focal depth.

Also provided by the subject invention are kits for practicing the subject methods, as described above. In one embodiment, the kit comprises: a) a population of particles each comprising a plurality of reactive tether molecules attached thereto; b) a capping agent, wherein said capping agent reacts with said reactive tether molecules to block them; and c) instructions to perform the following method: producing a dilution series of a capture agent, reacting each of the dilutions with a population of particles; and capping unreactive tether molecules on said particles after said particles have been reacted with the capture agents, thereby producing a population of particles comprising first particles that have a single reactive tether molecule and second particles that have a two reactive tether molecules. The various components of the kit may be present in separate containers or certain compatible components may be precombined into a single container, as desired.

In addition to above-mentioned components, a kit may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The following references are incorporated herein for all purposes: WO2011153211 and Halvorsen et al (Biophys. J. 2010 98: L53-L55), particularly for disclosure of methods for making measurements of off rates for interactions, suitable tethers, particle chemistry and compositions, and chemistries and reaction conditions for linking to a substrate.

The specificity of interaction is a function of the binding constant $K_a=[PT]/[P][T]$, where [P], [T], and [PT] are the molar concentrations of the unbound probe, the unbound target, and the bound duplex, respectively. The binding constant is related to the bimolecular on rate ($k_{on}$, in $M^{-1}s^{-1}$) and the unimolecular off rate ($k_{off}$, in $s^{-1}$) as $K_a=k_{on}/k_{off}$. To fully characterize the interaction, any two of the three parameters $K_a$, $k_{on}$, and $k_{off}$, should be measured.

Efficient direct measurement of off rates is practical if an external physical force is applied to the interacting molecules. Several such methods have been reported, using atomic force microscopy, magnetic or optical tweezers, or centrifugal force. In one method, the capture agents are covalently attached to one end of a long polymer tether, whose other end is covalently bound to the surface of a small (e.g. 5 μm) bead. The binding partners are covalently bound to the surface of a glass microscope slide. The functionalized beads are mixed with the slide in a sealed chamber, allowed to react, then washed, resealed with fresh buffer, and mounted on the end of a centrifuge arm observable through a microscope.

High throughput single-molecule force spectroscopy may be achieved by pulling the tethered particles directly away from the substrate. The centrifugal force applied to each molecular tether can be easily determined using $F=mu^2R$, where m is the mass of the bead (minus the mass of the medium displaced to account for buoyancy), u is the angular velocity, and R is its distance from the axis of rotation. For monodisperse beads of known size and density (available commercially or by processing) the centrifugal force on each particle is identical and can be calculated directly without calibration. This enables the detection of molecular transitions, such as bond rupture or tether extension such as a bi-molecular interaction. For example, one can determine the bond dissociation kinetics under constant force by measuring the times at which singly tethered beads abruptly detach from the substrate and disappear from view of the detector.

In order to make molecular binding measurements, a rotating high resolution video system can be employed, and a substrate that can be functionally derivatized with a defined binding partner. In this format, a substrate derivatized with a binding partner is enclosed in a small chamber containing the appropriate biochemical conditions and a capture agent linked to a particle is allowed to interact with the binding partner. After washing away unbound particles, the substrate is covered with fresh buffer, sealed, and subjected to increasing centrifugal force. The force-dependent unbinding kinetics for the binding pair can then be determined for many individual binding pairs in a single experiment. From these measurements, the off rate for the bi-molecular interaction can be determined.

Multiple cooperatively bound target-probe pairs are exponentially more difficult to dissociate than is a single target-probe pair, and that the exponent is related to the association rate $k_{on}$. Thus, the platform described above can be used to determine the on rate of an interaction, thereby allowing the bimolecular interaction to be fully characterized.

For binding measurements between a defined capture agent (e.g., a protein, metabolite or nucleic acid) and a ligand, the capture agent is attached to a particle, e.g., a bead through a flexible tether. The bead particles should be monodisperse and of sufficient diameter to generate the necessary force during the centrifugal measurement. The capture agent can be tethered via a DNA molecule to the bead using one of a number of approaches including direct covalent coupling through primary amines on the DNA and the protein or through the use of biotinylated DNA and streptavidin—protein ligand conjugates. In all cases, the coupling of the capture agent to the particle should not interfere with the interaction of the capture agent with the binding partner molecules that are present on the substrate surface.

Figure 2:
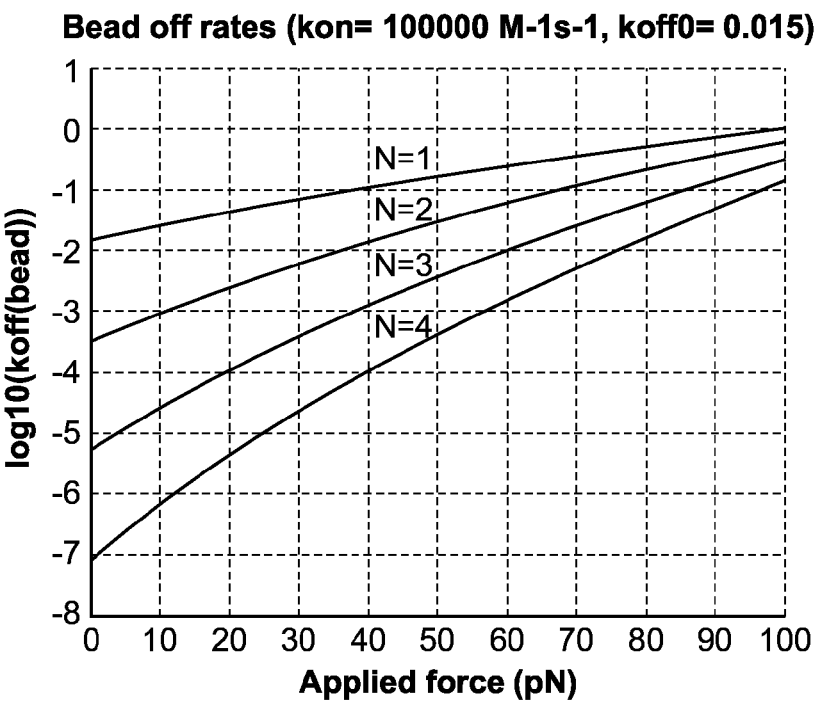
FIG. 2 is a graph showing simulated response curves of particles functionalized with one, two, three, or four tethered capture agents.

FIG. 2 shows a simulated response curve of a model system in which beads functionalized with one, two, three, or four tethered capture agents interact with surface-bound binding partners under increasing external force. In the modeled system, the off rate for a bead held by N cooperating target-probe pairs is roughly proportional to $k_{off}^N$ when no external force is applied, and at higher applied forces the off rates converge.

To perform a binding measurement, the substrate should be housed within a sealed chamber that allows for optical detection through the chamber by the vision system. In certain cases, the platform should accommodate chambers having different volumes (changing the dimension in the z axis—thickness of the solution over the microarray surface) ranging from about 50 to 5,000 microns. This will enable more flexibility in performing certain experiments in which the concentration of the capture agent is critical to the measurement. For a typical binding experiment, the beads are incubated with the substrate surface under buffer conditions that promote binding such that the surface is not fully saturated with bead-bound targets. The slide is then washed to remove unbound beads, and resealed with fresh buffer to measure the off rates. It is not necessary for the system to come to equilibrium prior to applying the centrifugal force. The force is then applied according to a force program as described below, and the beads are continuously monitored using the visualization system.

This method is based on cooperative binding and requires that the different particles be functionalized with different numbers of functionalized tethers simultaneously capable of reaching and reacting with the surface probes. One method of achieving this is to first cover the particle surface with bound polymer tethers having reactive ends, then allow these beads to react with a dilute solution of the capture agent, for a length of time such that the average capture agent coverage of each bead allows a single tethered capture agent to reach the surface at one time. The reaction is then quenched by deactivating the reactive ends of the tethers. A population of particles functionalized in this way may, after incubation with the surface binding partners, include some particles that are not bound to the substrate, some particles bound through a single capture agent-binding partner bond, some particles bound with two capture agent-binding partner bond, etc.

Figure 3:
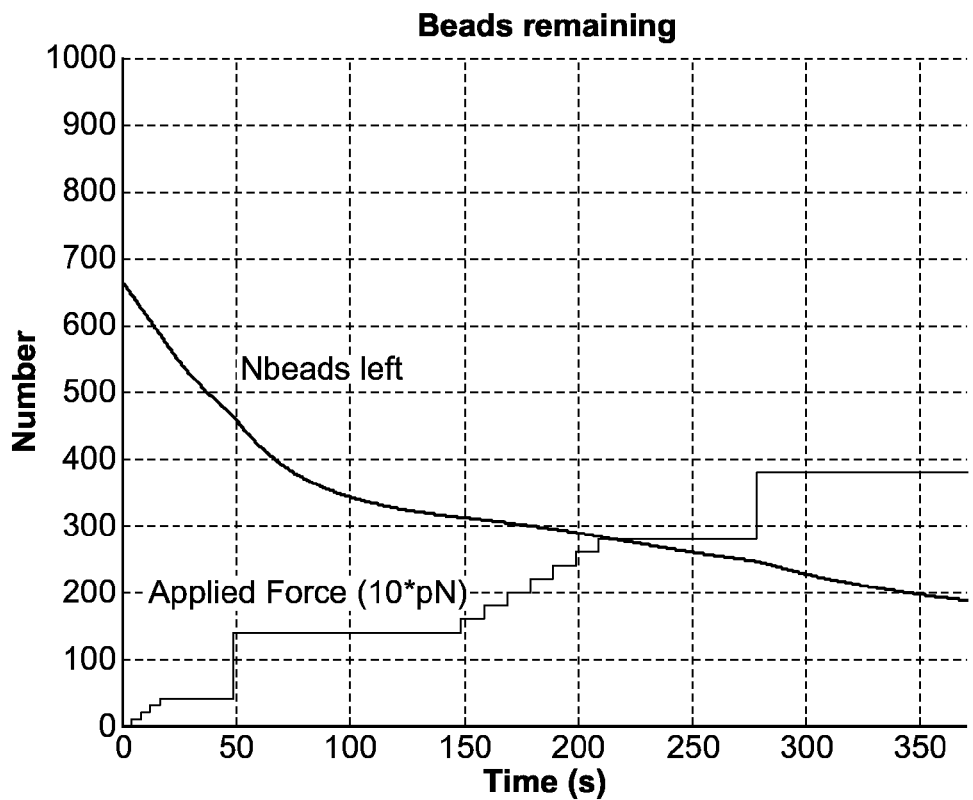
FIG. 3 is a graph showing the results of a simulation in which a slow force ramp is applied to the substrate.

In an exemplary embodiment, typical, a slow force ramp is applied to the substrate (results from this simulation are illustrated in FIG. 3). Those beads which are non-specifically bound are lost immediately (333/1000 beads in the simulation). At this point, only those beads that correspond to the specifically bound bead-tethered targets will remain in focus. The force is increased in slow steps until a specified fraction (e.g., 2%, at about 20 sec in this simulation) of the beads have been lost, held constant until another specified fraction is lost (e.g., 10%, at about 50 sec in this simulation). The force steps in this initial ramp are chosen such that few beads with more than one bound target will be lost. From this initial ramp, 1/T is measured, which allows an estimate of $k_{off}$ and $d \log(k_{off})/d$ force for a single capture agent-binding partner bond (i.e. $k_1$ in Equation 1). The applied force can be stepped up, and the $\log(k_{off})$ vs force curve can be extrapolated to estimate the length of time required to release 99% of the singly-bound beads (at about 150 sec in this simulation). At that point, another slow force ramp is begun, as beads bound by two probe-target pairs are separated loose.

Figure 4:
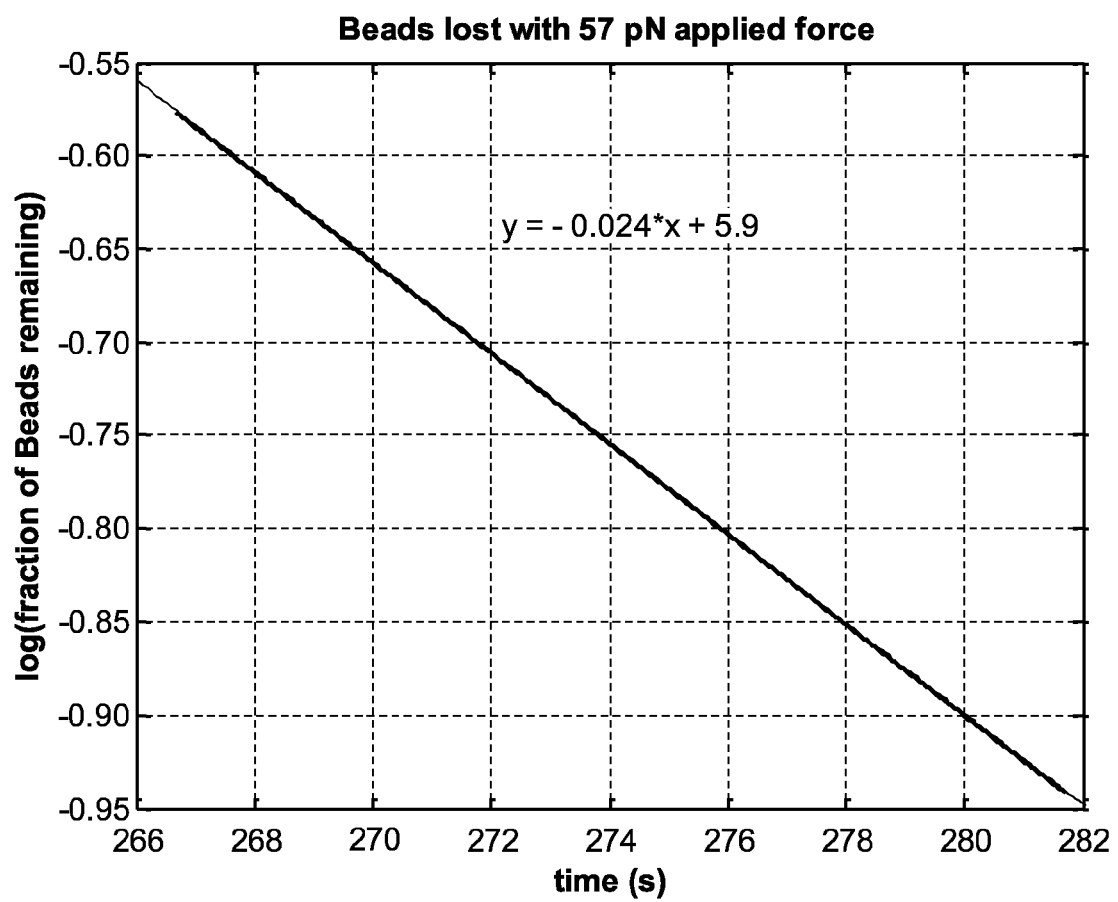
FIG. 4 is a graph showing how many beads are lost over time at 57 pN of applied force.

The coupled rate equations (Equation 1) can be solved in closed form, using methods known to the art. We will describe here the solutions for N=2 (i.e. two tethered capture agents on the bead), although the solutions for N>2 are similar. For stably bound capture agents, the on rate $k_2$ is fast compared with $k_{off}$, and the fraction of beads with two bound tethers $f_2 > f_1$ during most of the time the beads are being forced off. During this time, the off rate of the beads, given by $$kB_{off} = -(f_1' + f_2')/(f_1 + f_2) \tag{3}$$

is very nearly constant, and can be empirically observed as the rate at which beads initially bound with two tethers are lost from the surface. The on rate for reattachment is then:

$$k_{on} = (2k^2_{off} - 3k^2_{off} kB_{off} + kB^2_{off})/kB_{off}/c, \tag{4}$$

where the measurements of $k_{off}$ and $kB_{off}$ are made at an applied force in the linear range (see FIG. 4), and c is the effective molar concentration of probes accessible to the cooperating targets, which depends on the tether length and springiness, on the surface density of probes, and on the diameter of the bead. Notably, c does not depend on any characteristics of the capture agent or binding partners molecules being studied, and thus could be calibrated by measuring an interacting pair whose on and off rates are known from independent measurements.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for measuring a property of a binding interaction between a capture agent and a binding partner for said capture agent, comprising:
   a) contacting a population of particles that are linked to a capture agent with a substrate comprising a binding partner to produce capture agent/binding partner complexes, wherein said population of particles comprises first particles that are bound to a single molecule of said capture agent and second particles that are bound to two molecules of said capture agent;
   b) applying a force to the particles, wherein said force is in a direction that separates said particles from said substrate;
   c) separately measuring:
      (i) the force required to disassociate the first particles from their respective complexes and
      (ii) the force required to dissociate the second particles from their respective complexes;
   d) calculating the off rates of said first particles and said second particles as a function of the applied force;
   e) calculating the off rate for said first particles in the absence of applied force from the dependence of off rates on the applied force; and f) calculating the on rates for binding said first particles and said second particles, using the respective off rates calculated in d) and e).

2. The method of claim 1, wherein said force is a centrifugal force.

3. The method of claim 1, wherein said force is a magnetic force.

4. The method of claim 1, wherein said applying comprises increasing said force over a period of time, and observing the release of said particles from said support.

5. The method of claim 1, wherein said particles are of a defined size and density.

6. The method of claim 1, wherein said particles are made of borosilicate glass, polystyrene, silica, gold, melamine or iron oxide.

7. The method of claim 1, wherein said particles are linked to said capture agent via a flexible tether.

8. The method of claim 1, wherein said on rate is calculated by using the following formula:

$$k_{on}=(k_{off}-kB_{off})^2/kB_{off}/c$$

wherein $k_{off}$ and $kB_{off}$ are the off rates of the first and second particles and c is the molar concentration of binding partner accessible to capture agents on a particle.

9. The method of claim 1, wherein said capture agent is a protein or nucleic acid.

10. The method of claim 1, wherein said binding partner is a protein or nucleic acid.

11. The method of claim 1, wherein said substrate comprises a nucleic acid array.

* * * * *

UNITED STATES PATENT AND TRADEMARK OFFICE
CERTIFICATE OF CORRECTION

PATENT NO. : 9,182,334 B2
APPLICATION NO. : 13/758708
DATED : November 10, 2015
INVENTOR(S) : Bo Curry Page 1 of 1

It is certified that error appears in the above-identified patent and that said Letters Patent is hereby corrected as shown below:

Drawings

On sheet 2 of 3, in Figure 2, line 1, delete "(kon=100000 M-1s-1, koff0=0.015)" and insert -- ($k_{on}$=100000 M-1s-1, $k_{off}$0=0.015) --, therefor.

On sheet 2 of 3, in Figure 2, line 1 (Y-Axis), delete "log10(koff(bead))" and insert -- log10($k_{off}$(bead)) --, therefor.

Specification

In column 2, line 41, delete "band" and insert -- 6 and --, therefor.

In column 3, line 29, delete "velocity w" and insert -- velocity ω --, therefor.

In column 5, line 36, delete "phosphoramadite" and insert -- phosphoramidite --, therefor.

In column 5, line 50, delete "6,023,540) To" and insert -- 6,023,540). To --, therefor.

In column 6, line 14, delete "known it" and insert -- known. It --, therefor.

In column 6, line 30, delete "velocity w." and insert -- velocity ω. --, therefor.

In column 6, line 42, delete "velocity w." and insert -- velocity ω. --, therefor.

In column 7, line 22, delete "speed w" and insert -- speed ω --, therefor.

Signed and Sealed this
Twelfth Day of July, 2016

Michelle K. Lee
*Director of the United States Patent and Trademark Office*